United States Patent
Weiss et al.

(10) Patent No.: US 11,583,572 B2
(45) Date of Patent: Feb. 21, 2023

(54) ENCAPSULATION OF ULTRA-STABLE INSULIN ANALOGUES WITH POLYMER MELTS

(71) Applicant: CASE WESTERN RESERVE UNIVERSITY, Cleveland, OH (US)

(72) Inventors: Michael Weiss, Moreland Hills, OH (US); Jonathan Pokorski, Cleveland, OH (US)

(73) Assignee: Case Western Reserve University, Cleveland, OH (US)

( * ) Notice: Subject to any disclaimer, the term of this patent is extended or adjusted under 35 U.S.C. 154(b) by 980 days.

(21) Appl. No.: 16/065,596

(22) PCT Filed: Dec. 23, 2016

(86) PCT No.: PCT/US2016/068572
§ 371 (c)(1),
(2) Date: Jun. 22, 2018

(87) PCT Pub. No.: WO2017/112952
PCT Pub. Date: Jun. 29, 2017

(65) Prior Publication Data
US 2021/0162014 A1 Jun. 3, 2021

Related U.S. Application Data

(60) Provisional application No. 62/387,459, filed on Dec. 23, 2015.

(51) Int. Cl.
*A61K 38/28* (2006.01)
*A61K 9/00* (2006.01)
*A61P 3/10* (2006.01)
*C07K 14/62* (2006.01)

(52) U.S. Cl.
CPC ............ *A61K 38/28* (2013.01); *A61K 9/0021* (2013.01)

(58) Field of Classification Search
CPC ........ A61K 38/28; A61K 9/0021; A61K 9/00; A61K 9/146; A61P 3/10; C07K 14/62
See application file for complete search history.

(56) References Cited

U.S. PATENT DOCUMENTS

| | | | |
|---|---|---|---|
| 11,174,303 B2* | 11/2021 | Weiss | A61P 5/48 |
| 2011/0195896 A1 | 8/2011 | Weiss et al. | |
| 2013/0034602 A1* | 2/2013 | Qian | A61K 9/1647 424/456 |
| 2013/0172247 A1 | 7/2013 | Ludvigsen et al. | |
| 2014/0323398 A1 | 10/2014 | Weiss | |
| 2015/0274803 A1 | 10/2015 | Weiss | |
| 2018/0265560 A1* | 9/2018 | Weiss | C07K 14/62 |

FOREIGN PATENT DOCUMENTS

| | | |
|---|---|---|
| JP | 2013530702 | 8/2013 |
| WO | 2005054291 | 6/2005 |
| WO | 2007081824 | 7/2007 |
| WO | 2007096332 | 8/2007 |
| WO | 2009132129 | 10/2009 |
| WO | 2010014946 | 2/2010 |
| WO | 2011161124 | 12/2011 |
| WO | 2011161125 | 12/2011 |
| WO | 2013010048 | 1/2013 |
| WO | 2013010048 A2 | 1/2013 |
| WO | 2014071405 | 5/2014 |
| WO | 2015010927 | 1/2015 |

OTHER PUBLICATIONS

Harris et al., "Effect of PEGylation on Pharmaceuticals," Nature, Mar. 2003, 2: 214-221. (Year: 2003).*
Vinther, Tine N. et al., "Insulin analog with additional disulfide bond has increased stability and preserved activity," Protein Science, Dec. 26, 2012, pp. 296-305, vol. 22.
Hua, Qing-xin et al., "Design of an Active Ultrastable Single-chain Insulin Analog," The Journal of Biological Chemistry, May 23, 2008, pp. 14703-14716, vol. 283, No. 21.
Vinther T.N. et al., "Insulin analog with additional disulphide bond has increased stability and preserved activity", Protein Science, 2013, vol. 22, pp. 296-305.
Vinther T.N. et al., "Additional disulphide bonds in insulin: Prediction, recombinant expression, receptor binding affinity, and stability", Protein Science, Jan. 2015, vol. 24, pp. 779-788.
Weiss M.A., "Design of ultra-stable insulin analogues for the developing world", Journal of Health Specialties, Jul. 2013, vol. 1, Issue 2, pp. 59-70.
Hua, Q.-X. et al., "Design of an Active Ultrastable Single-chain Insulin Analog", The Journal of Biological Chemistry, 2008, vol. 283, No. 21, pp. 14703-14716.

(Continued)

*Primary Examiner* — Julie Ha
(74) *Attorney, Agent, or Firm* — Hahn Loeser & Parks, LLP; John J. Cunniff

(57) ABSTRACT

An insulin composition comprises an insulin analogue and polymer blend. The insulin analogue contains cysteine substitutions at positions B4 and A10 (to form cystine B4-A10), and one or more additional substitutions selected from the group consisting of: a connecting domain of 5-11 amino acids between insulin A- and B domains; a non-beta-branched amino-acid substitution at position A8; a non-beta-branched acidic or polar side chain at position A14; a halogenic modification of PheB24 at the ortho position; and substitution of lysine at position B29 by Glu, Ala, Val, Ile, Leu, amino-propionic acid, amino-butryic acid, or Norleucine. The insulin analogue is compatible with a process of manufacture that includes one or more steps within the temperature range 90-120° C. The encapsulated insulin analogue may optionally contain free PEG or be PEGylated. The insulin analogue-encapsulated polymer blend may be cast as a microneedle patch for topical administration or as micropellets for subcutaneous injection.

15 Claims, 7 Drawing Sheets
Specification includes a Sequence Listing.

(56) References Cited

OTHER PUBLICATIONS

Lee P. et al., "PEGylation to Improve Protein Stability During Melt Processing", Macromolecular Bioscience, Oct. 2015, vol. 15, No. 10, pp. 1332-1337.
International Search Report and Written Opinion for PCT/US2016/068572.
Anand, Om et al., "Controlled Release of Modified Insulin Glargine from Novel Biodegradable Injectable Gels," AAPS PharmiSciTech, vol. 13, No. 1, Mar. 2012.
Om Anand et al., "Controlled Release of Modified Insulin Glargine from Novel Biodegradable Injectable Gels," AAPS PharmSciTech, Mar. 1, 2012, pp. 313-322, vol. 13, No. 1, United States.

* cited by examiner

PROINSULIN

MODEL

ENCAPSULATION OF ULTRA-STABLE INSULIN ANALOGUES WITH POLYMER MELTS

CROSS REFERENCE TO RELATED APPLICATIONS

This application claims benefit of U.S. Provisional Application No. 62/387,459 filed on Dec. 23, 2015.

STATEMENT REGARDING FEDERALLY SPONSORED RESEARCH OR DEVELOPMENT

This invention was made with government support under grant numbers DK040949 and DK074176 awarded by the National Institutes of Health and by grant number DMR0423914 awarded by the National Science Foundation. The U.S. government has certain rights in the invention.

BACKGROUND OF THE INVENTION

This invention relates to polymer encapsulation of polypeptide hormone analogues that exhibits enhanced thermal and thermodynamic stability, including augmented resistance to aggregation-coupled misfolding and thermal fibrillation above room temperature. Such enhanced stability enables the hormone analogues to maintain activity following a manufacturing process with steps requiring temperatures in the range 90-120° C. More particularly, this invention relates to encapsulation with a polymer melt of ultra-stable insulin analogues consisting of a two of more stabilizing elements, one of which is an additional disulfide bridge between residues B4 and A10. The second element consists of one or more elements selected from the group: (a) a foreshortened connecting (C) domains between A and B domains; (b) a non-beta-branched amino-acid substitution at α-helical C-CAP position A8; (c) a non-beta-branched acidic or polar side chain at A14; (d) a halogenic modification of the aromatic ring of $Phe^{B24}$ at the ortho position (ring position 2 of 6; halogen chosen from the group Fluorine, Chlorine or Bromine) of the aromatic side chain; and/or (e) substitution of $Lys^{B29}$ by Arginine, Glutamic Acid or a natural amino acid with a neutral aliphatic side chain (selected from the group Ala, Val, Ile, or Leu) or unnatural amino-acid side chain with a neutral aliphatic side chain (amino-propionic acid, amino-butryic acid, or norleucine). Optionally, in either two-chain or single-chain analogues, N-terminal residues (comprising residue B1, residues B1 and B2, or residues B1-B3) may be deleted from the B chain (or B domain), and also $Asn^{A21}$ may optionally be substituted by Asp, Ala, Gly or Ser. The N-terminus of the SCI, A chain or B chain may optionally be modified by PEGylation as described to ensure a more uniform distribution in the polymer blend (Lee, P., et al. *Macromol. Biosci.* 15:1332-7 (2015))

Administration of insulin has long been established as a treatment for diabetes mellitus. A major goal of conventional insulin replacement therapy in patients with diabetes mellitus is control of the blood glucose concentration to prevent its excursion above or below the normal range characteristic of healthy human subjects. Excursions below the normal range are associated with immediate adrenergic or neuroglycopenic symptoms, which in severe episodes lead to convulsions, coma, and death. Excursions above the normal range are associated with increased long-term risk of microvascular disease, including retinopathy, blindness, and renal failure. Whereas the treatment of Type 1 diabetes mellitus ordinarily requires a combination of a basal insulin formulation (or long-acting insulin analogue formulation) and a prandial insulin formulation (or rapid-acting insulin analogue formulation) as administered by subcutaneous injection, in many cases Type 2 diabetes mellitus may be treated only with a basal insulin formulation (or long-acting insulin analogue formulation). The present invention pertains to such basal insulin therapy.

Insulin is a small globular protein that plays a central role in metabolism in vertebrates. Insulin contains two chains, an A chain, containing 21 residues, and a B chain containing 30 residues. The hormone is stored in the pancreatic β-cell as a $Zn^{2+}$-stabilized hexamer, but functions as a $Zn^{2+}$-free monomer in the bloodstream. Insulin is the product of a single-chain precursor, proinsulin, in which a connecting region (35 residues) links the C-terminal residue of B chain (residue B30) to the N-terminal residue of the A chain (FIG. 1A). A variety of evidence indicates that it consists of an insulin-like core and disordered connecting peptide (FIG. 1B). Formation of three specific disulfide bridges (A6-A11, A7-B7, and A20-B19; FIGS. 1A and 1B) is thought to be coupled to oxidative folding of proinsulin in the rough endoplasmic reticulum (ER). Proinsulin assembles to form soluble $Zn^{2+}$-coordinated hexamers shortly after export from ER to the Golgi apparatus. Endoproteolytic digestion and conversion to insulin occurs in immature secretory granules followed by morphological condensation. Crystalline arrays of zinc insulin hexamers within mature storage granules have been visualized by electron microscopy (EM). The sequence of insulin is shown in schematic form in FIG. 1C. Individual residues are indicated by the identity of the amino acid (typically using a standard three-letter code), the chain and sequence position (typically as a superscript). Pertinent to the present invention is the invention of novel foreshortened C domains of length 6-11 residues in place of the 36-residue wild-type C domain characteristic of human proinsulin.

Insulin and conventional insulin analogues in liquid- or microcrystalline formulations are susceptible to both physical degradation and chemical degradation. Whereas physical degradation leads to formation of fibrils, chemical degradation involves the breakage of chemical bonds with loss of rearrangement of atoms within the molecule or the formation of chemical bonds between different insulin molecules. Physical and chemical degradation is markedly accelerated above room temperature and even more so above 55° C. Such degradation impairs biological activity. The susceptibility of insulin and conventional insulin analogues in liquid- or microcrystalline formulations to various forms of degradation currently prevents their encapsulation within polymer melts requiring one or more manufacturing steps in the temperature range 90-120° C. An example of such a polymer melt is provided by poly(lactic-co-glycolic acid (PL-GA; at various molecular ratios, including but not restricted to 50:50), which may be ground to a powder via ball mill or mortar and pestle and mixed with lyophilized SCI (or conventional two-chain insulin analogs) in the solid state. The blended powder (loaded with an ultra-stable insulin analogue) can be extruded in a melt process in the temperature range 90-120° C. for at least 10 min and solidified at room temperature. Such polymer melts can be casted into a variety of shapes, including sheets containing microneedles for application to the skin and micropellets for subcutaneous injection. PL-GA is known in the art to be non-toxic and to undergo slow dissolution to non-toxic breakdown products in the body, making possible its use in a variety of medical devices and pharmaceutical delivery systems (see Ahmed, T. (2015); Ortega-Oller, I., et al. (2015); and Rahimian, S., et al. (2015)). It use in medical devices has thus been approved by the United States Food & Drug Administration.

The present invention was motivated by medical and societal needs to engineer a basal once-a-week, bimonthly or once-a-month method of insulin analogue delivery to improve the convenience, safety and efficacy of insulin replacement therapy for the treatment of diabetes mellitus.

SUMMARY OF THE INVENTION

It is, therefore, an aspect of the present invention to provide a polymer melt of a two-chain or single-chain insulin analogue that possesses sufficient thermal and thermodynamic stability to maintain biological activity following a process of manufacture that includes one or more obligatory steps within the temperature range 90-120° C. More particularly, this invention relates to encapsulation with a polymer melt of ultra-stable insulin analogues consisting of a two of more stabilizing elements, one of which is an additional disulfide bridge between residues B4 and A10. The second element consists of one or more elements selected from the group: (a) a foreshortened connecting (C) domains between A and B domains; (b) a non-beta-branched amino-acid substitution at a-helical C-CAP position A8; (c) a non-beta-branched acidic or polar side chain at A14; (d) a halogenic modification of the aromatic ring of $Phe^{B24}$ at the ortho position (ring position 2 of 6; halogen chosen from the group Fluorine, Chlorine or Bromine) of the aromatic side chain; and/or (e) substitution of $Lys^{B29}$ by Glutamic Acid or a natural amino acid with a neutral aliphatic side chain (selected from the group Ala, Val, Ile, or Leu) or unnatural amino-acid side chain with a neutral aliphatic side chain (amino-propionic acid, amino-butryic acid, or norleucine). Optionally, in either two-chain or single-chain analogues, residues B1 or B2 may be deleted from the B chain (or B domain), and also $Asn^{A21}$ may optionally be substituted by Asp, Ala, Gly or Ser.

The analogues of the present invention contain Histidine at position B10 and so circumvent concerns regarding carcinogenesis that is associated with an acidic substitution (Aspartic Acid or Glutamic Acid) at this position. It is an additional aspect of the present invention that absolute in vitro affinities of the two-chain or single-chain insulin analogue for IR-A and IR-B are in the range 5-150% relative to wild-type human insulin and so unlikely to exhibit significantly prolonged residence times in the hormone-receptor complex.

The present invention thus envisions encapsulation within a polymer melt of insulin analogues that consist of two polypeptide chains (designated A and B) connected by three disulfide bridges (native bridges B7-A7, B19-A20, an engineered bridge B4-A10; and in addition cystine A6-A11 within the A chain) containing one or more of modifications (b-e). Alternatively, the scope of the present invention includes polymer-melt encapsulation of single-chain insulin analogues (SCIs) containing four disulfide bridges (B4-A10, B7-A7, B19-A20, and A6-A11) and one or more of modifications (a-e). The SCIs contain a foreshortened connection domain of length 5-11 residues whose N-terminal two residues contain at least one acidic residue. The two-chain or single-chain insulin analogues contained with the polymer melts of the present invention may optionally contain standard or non-standard amino-acid substitutions at other sites in the A or B domains.

The feasibility of a fourth disulfide bridge per se between positions B4 and A10 (as defined in wild-type two-chain insulin) is not known in the art in the context of an active SCI. An insulin analogue containing such a fourth disulfide bridge is also not known, in either two-chain or single-chain analogues, in combination with another stabilizing element for the purpose of polymer encapsulation.

The engineering of non-standard proteins, including therapeutic agents and vaccines, may have broad medical and societal benefits. Naturally occurring proteins—as encoded in the genomes of human beings, other mammals, vertebrate organisms, invertebrate organisms, or eukaryotic cells in general—often confer multiple biological activities. A benefit of non-standard proteins would be to achieve sufficient thermal and thermodynamic stability to permit encapsulation within a polymer melt, without loss of biological activity, whose process of manufacture contains one or more steps within the temperature range 90-120° C. Yet another example of a societal benefit would be the use of such insulin analogue-containing polymer melts to facilitate the transport, distribution, and use of such polymer melts for the treatment of diabetes mellitus in human patients or in other mammals, such as (but not limited to) dogs or cats with diabetes mellitus. The insulin analogue-containing polymer melts may be fabricated into microneedle patches applied to the skin such that the slow dissolution of the microneedles provides a long-term method of subcutaneous insulin administration for a period of at least one week and optionally for periods of up to one month. Alternatively, the insulin analogue-containing polymer melts may be fabricated into injectable dissolvable micropellets for subcutaneous injection; their slow dissolution within the subcutaneous space would likewise provide a slow-release depot of insulin for at least one week and optionally up to one month.

The societal benefit of the present invention would be especially marked in regions of the developing world where electricity and refrigeration are not consistently available. The challenge posed by the physical degradation of liquid and microcrystalline formulations of insulin and insulin analogues was first recognized in the 1930s. The severity of this challenge has been deepened in the past decade by the pending epidemic of diabetes mellitus in Africa and Asia. The polymer encapsulation of ultra-stable two-chain insulin analogues or ultra-stable SCIs containing a fourth disulfide bridge between positions B4 and A10 in combination with at least one other stabilizing element, may enhance the safety and efficacy of insulin replacement therapy in such challenged regions.

DETAILED DESCRIPTION OF THE INVENTION

Figure 1A:
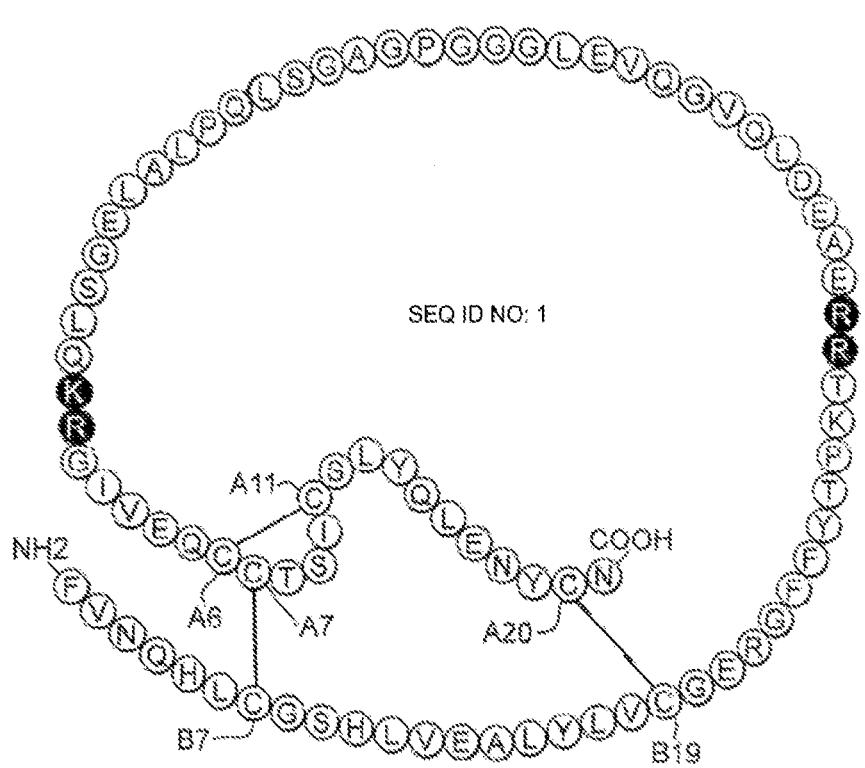
FIG. 1A is a schematic representation of the sequence of human proinsulin (SEQ ID NO: 1) including the A- and B-chains and the connecting region shown with flanking dibasic cleavage sites (filled circles) and C-peptide (open circles).
Figure 1B:
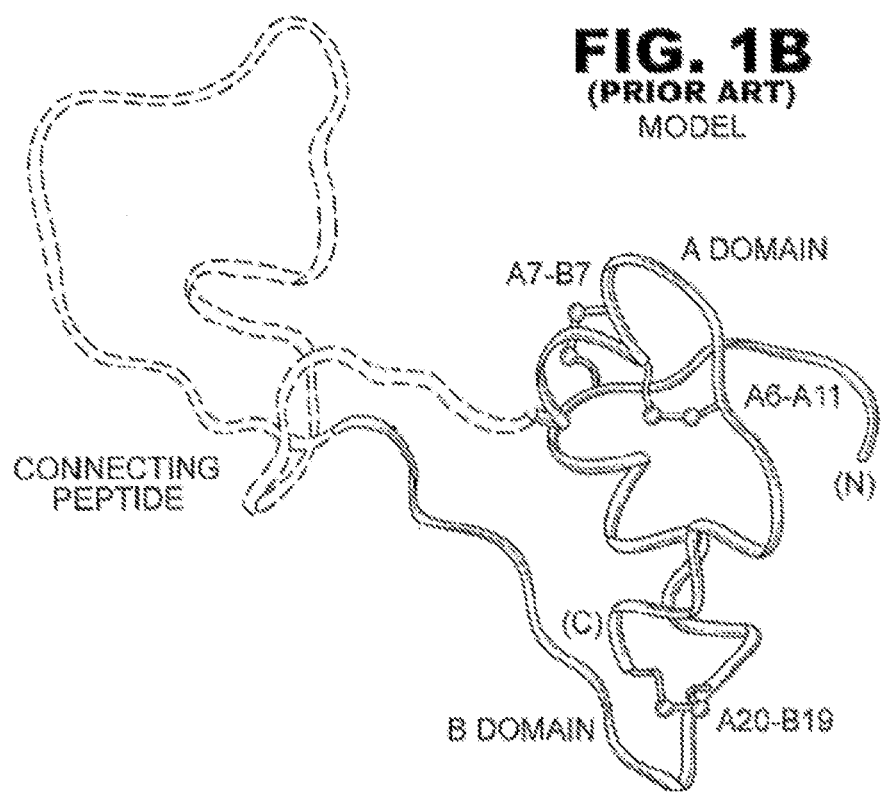
FIG. 1B is a structural model of proinsulin, consisting of an insulin-like moiety and a disordered connecting peptide (dashed line).
Figure 1C:
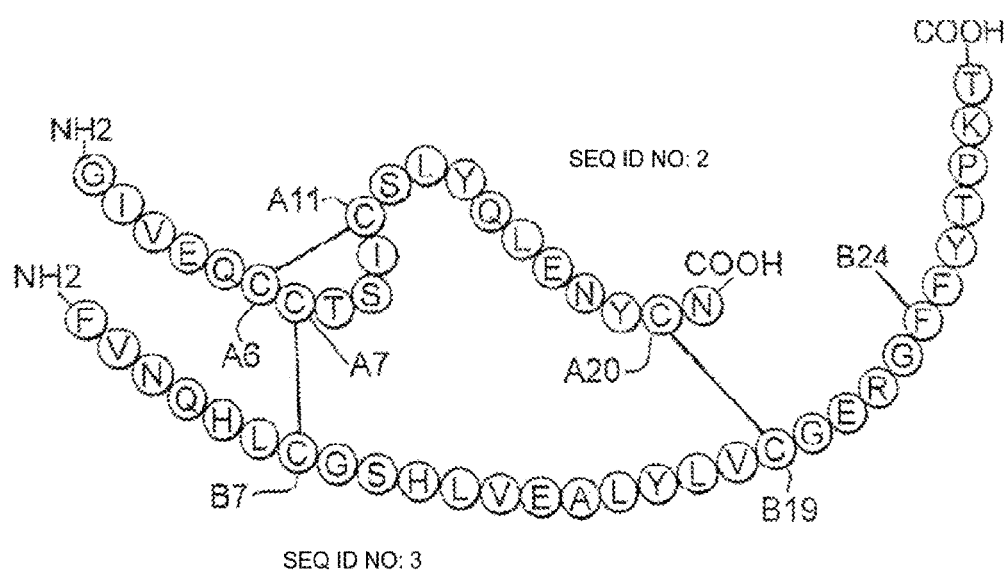
FIG. 1C is a schematic representation of the sequence of wild type human insulin A-Chain (SEQ ID NO:2) and B-Chain (SEQ ID NO:3) indicating the location of the disulfide bridges and the position of residue B24 in the B-chain.

The present invention is directed toward compositions containing polymer melts of a two-chain or single-chain insulin analogue that exhibits so marked an increase in thermal and thermodynamic stability that it may be subjected to a polymer melt process within the temperature range 90-120° C. for at least ten minutes (a) without loss of biological activity on dissolution of the polymer within the dermis or within the subcutaneous space of a mammal or (b) without loss of biological activity on dissolution of the polymer in vitro in a physiological buffer or on a dilute acidic solution on incubation with gentle agitation at 37° C.

It is a feature of the present invention that the isoelectric point of the insulin analogues may either (i) be in the range 3.0-6.0 so as to permit a soluble manufacturing intermediate as a solution at neutral pH or (ii) be in the range 6.5 and 8.0 such that a soluble formulation may be obtained under acidic conditions (pH 3.0-5.5). The latter analogues, when released in the body from a polymer melt, would be expected to undergo isoelectric precipitation in the subcutaneous depot due to a shift of pH to near neutrality. Such precipitation could enhance the safety of a polymeric device in the advent that one or more microneedles or micropellets dissolve suddenly or more rapidly than expected based on the bulk properties of the parent polymer melts.

In one embodiment, the polymer may be selected from the group consisting of Poly(lactic-co-glycolic acid) (PLGA), Poly(caprolactone), Polylactic acid, Polyglycolic acid, Poly (hydroxybutyric acid), chitosan, poly(sebacic acid), polyanhydrides, polyphosphazenes, poly(orthoesters, Poly (lactic acid-co-caprolactone), Poly(hydroxybutyrate-valerate) and mixtures and copolymers thereof. In addition or in the alternative, porogens such as polyethylene glycol, NaCl and/or sugars may optionally also be present to regulate the rate of release of insulin from the polymer composition.

The polymer molecular weight may be chosen according to the requirements of a particular application and the desired rate of release of insulin. In one embodiment, the polymer molecular weight, such as the molecular weight of polyethylene glycol, may have an average molecular weight less than 200 daltons, between 200 and 1000 daltons, between 1000 and 4500 daltons, between 4500 and 9000 daltons, between 9000 and 15000 daltons, between 15000 daltons and 25000 daltons, or greater than 25000 daltons. In one particular embodiment, PEG of about 8000 daltons may be used.

It is envisioned that single-chain or two-chain insulin analogues may be made with A- and B-chain sequences derived from animal insulins, such as porcine, bovine, equine, and canine insulins, by way of non-limiting examples. In addition or in the alternative, the insulin analogue of the present invention may contain a deletion of residue B1, residues B1-B2, or residues B1-B3 or may be combined with a variant B chain lacking Lysine to avoid Lys-directed proteolysis of a precursor polypeptide in yeast biosynthesis in *Pichia pastoris, Saccharomyces cerevisiae*, or other yeast expression species or strains. While not wishing to be constrained by theory, we envision that non-beta-branched substitutions at position A8 would protect the two-chain insulin analogues and SCIs from both physical and chemical degradation due to their more optimal properties within an alpha-helix and/or at the C-terminal position of an alpha-helix. Examples of stabilizing A8 substitutions are provided by, but not limited to, Arginine, Glutamic Acid and Histidine. While not wishing to be constrained by theory, we envision that charged or polar non-beta-branched substitutions at position A14 would protect the two-chain insulin analogues and SCIs from both physical and chemical degradation due to mitigation of the reverse-hydrophobic effect associated with solvent exposure of $Tyr^{A14}$ in wild-type human insulin. Among the proscribed set of stabilizing elements, we also envision that a halogen modification at the 2 ring position of $Phe^{B24}$ (i.e., ortho-F-$Phe^{B24}$, ortho-Cl-$Phe^{B24}$, or ortho-Br-$Phe^{B24}$; intended to enhance thermodynamic stability and resistance to fibrillation) provides a molecular mechanism that protects from both chemical degradation and physical degradation. We likewise envision that removal of the naturally occurring positive charge at position B29 (as provided by $Lys^{B29}$) would incrementally enhance the resistance of a two-chain insulin analogue containing cystine B4-A10 or of an SCI containing cystine B4-A10 to fibrillation at elevated temperatures. The B29 substitution may be Glutamic Acid or a neutral aliphatic standard or non-standard amino acid. A standard neutral aliphatic residue would be chosen from the group consisting of Ala, Val, Ile, or Leu; a nonstandard such residue would be chosen from the group amino-propionic acid, amino-butyric acid, or norleucine).

Furthermore, in view of the similarity between human and animal insulins, and use in the past of animal insulins in human patients with diabetes mellitus, it is also envisioned that other minor modifications in the sequence of insulin may be introduced, especially those substitutions considered "conservative." For example, additional substitutions of amino acids may be made within groups of amino acids with similar side chains, without departing from the present invention. These include the neutral hydrophobic amino acids: Alanine (Ala or A), Valine (Val or V), Leucine (Leu or L), Isoleucine (Ile or I), Proline (Pro or P), Tryptophan (Trp or W), Phenylalanine (Phe or F) and Methionine (Met or M). Likewise, the neutral polar amino acids may be substituted for each other within their group of Glycine (Gly or G), Serine (Ser or S), Threonine (Thr or T), Tyrosine (Tyr or Y), Cysteine (Cys or C), Glutamine (Glu or Q), and Asparagine (Asn or N). Basic amino acids are considered to include Lysine (Lys or K), Arginine (Arg or R) and Histidine (His or H). Acidic amino acids are Aspartic acid (Asp or D) and Glutamic acid (Glu or E). Unless noted otherwise or wherever obvious from the context, the amino acids noted herein should be considered to be L-amino acids. Standard amino acids may also be substituted by non-standard amino acids belong to the same chemical class. By way of non-limiting example, the basic side chain Lys may be replaced by basic amino acids of shorter side-chain length (Ornithine, Diaminobutyric acid, or Diaminopropionic acid). Lys may also be replaced by the neutral aliphatic isostere Norleucine (Nle), which may in turn be substituted by analogues containing shorter aliphatic side chains (Aminobutyric acid or Aminopropionic acid).

Figure 2:
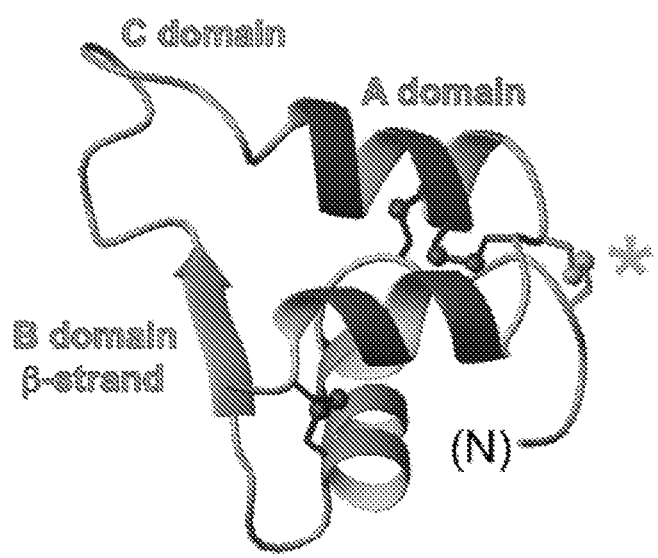
FIG. 2. 3D model of an SCI stabilized by a fourth disulfide bridge. The asterisk indicates B4-A10 disulfide bridge. The corresponding engineered cystine in a two-chain insulin analogue (i.e., between positions B4 and A10 in the two individual polypeptide chains) may be combined with at least one additional stabilizing modification at position A8, A14, B24 or B29.

By way of example, protein-PG-LA polymer blends were prepared containing insulin lispro (SEQ ID NOs: 2 and 13), an analogue of lispro insulin ($Lys^{B28}$, $Pro^{B29}$-human insulin) additionally containing $Cys^{A10}$, $Cys^{B4}$ substitutions (SEQ ID NOs: 2 and 14), an SCI of 59 amino-acid residues (SEQ ID NO: 9) and a corresponding 59-mer SCI modified with $Cys^{A10}$, $Cys^{B4}$ substitutions to contain the fourth disulfide bridge between residues B4 and A10 (SEQ ID NO: 10). These SCI contained a C domain of sequence EEGSRRSR. The A domain was modified at A8 to contain Arginine instead of Threonine. The B domain was modified to contain Arginine instead of Lysine to avoid protease digestion in the yeast Pichia pastoris. The isoelectric point of this SCI thus lies in the range 6.5-7.5 but is readily soluble in the pH range 2-4. Its affinity for the A- and B isoforms of the insulin receptor lies within the range 10-150% relative to wild-type human insulin, whereas its affinity for the Type 1 IGF receptor is tenfold lower than that of wild-type insulin. A three-dimensional model of this SCI and the predicted position of cysteine B4-A10 is shown in FIG. 2.

Figure 3:
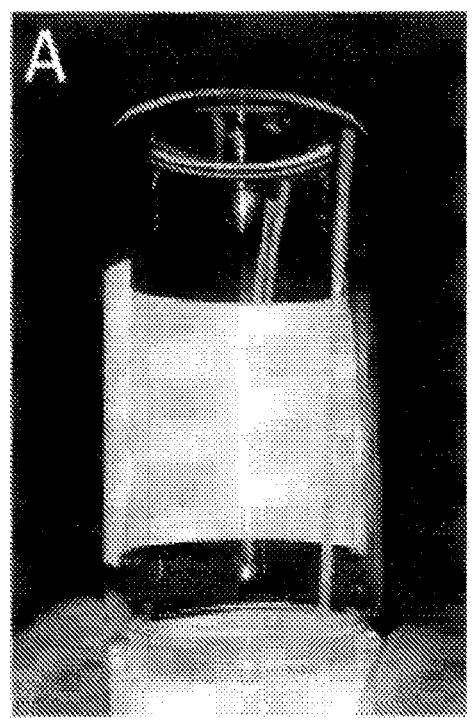
FIG. 3A is a photograph of a vial containing protein-polymer blends of modified insulin including a SCI with fourth disulfide bridge blend strips (thumb/finger at bottom for scale)
FIG. 3B is a graph showing blood glucose levels of rats in response to recovered SCI not containing a fourth disulfide bridge from the protein-polymer blends shown in FIG. 3A.
FIG. 3C is a graph showing blood glucose levels of rats in response to recovered modified SCI containing the fourth disulfide bridge from the protein-polymer blends shown in FIG. 3A.
Figure 3:
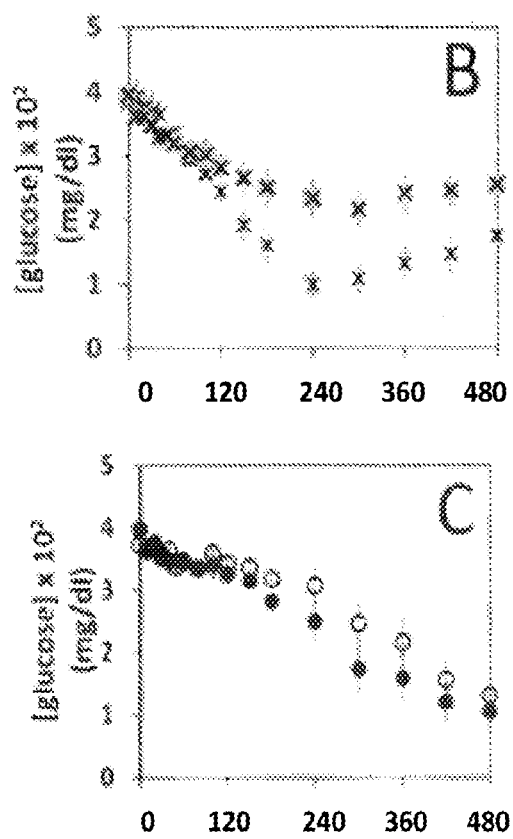

The above three polymer blends were cast in strips (FIG. 3A). The polymers were dissolved over 2 days in 0.01% trifluoroacetic acid at 20° C. to assess potential recovery of functional hormone. Whereas no active lispro was recovered, rat testing demonstrated ~40% recovery of the SCI (FIG. 3B) and essentially complete recovery of functional modified SCI containing the fourth disulfide bridge (FIG. 3C). The robustness of this "hyper-stable" insulin analogue to high-temperature protein-polymer blend extrusion is of exceptional promise as a technology to provide a long-term dissolvable therapeutic polymer blend for the treatment of diabetes mellitus. It should be noted that in this example utilizes a single-chain insulin analogue that exhibits an isoelectric point of near pH 7.4. This indicates that it is possible to take advantage of its basal PK/PD properties as a future safety mechanism: should a micro-needle crumble and dissolve rapidly subcutaneously, the released analogue would undergo precipitation, avoiding acute hypoglycemia.

Elution of insulin analogue protein from a polymer melt in phosphate buffered saline (PBS) at pH 7.4 was also examined. Test cylindrical polymers were prepared with 50%-50% PLGA containing 25% weight/weight of a single-chain insulin (SCI) analogue stabilized by a fourth disulfide bridge between residues B4 and A10. The analogue (designated 4SS-81-06; SEQ ID NO: 12) contains a six-residue linker of sequence EEGPRR, two substitutions in the A domain (substitution of $Thr^{A8}$ by His and substitution of $Tyr^{A14}$ by Glu) and one substitution in the B domain (substitution of $Lys^{B29}$ by Glu). The mixed powder was heated to 95 degrees centigrade for 10 minutes and then extruded rapidly by force through using a special syringe extruder. The extruded polymeric cylinders (1 mm diameter and 8 mm in length; 10 mg) were prepared using mixtures of PL, GA and SCI powders containing 0, 5 or 10% polyethylene glycol (PEG; mean molecular mass 8 kDa). To test the effect of the free PEG molecule on the rate of release of the SCI from the polymer, the cylinders were placed in phosphate-buffered saline at pH 7.4 and 37° C. with gentle rocking with daily replacement of the buffer. 500 microliters of solution was collected daily and replaced with 500 uL of fresh PBS with (0.1%) sodium azide. Polymer was placed in solution during the afternoon of day 0 and samples were collected roughly every 24 hours after. The day 0 sample was collected immediately (<5 minutes) after polymer was immersed in solution.

Figure 4:
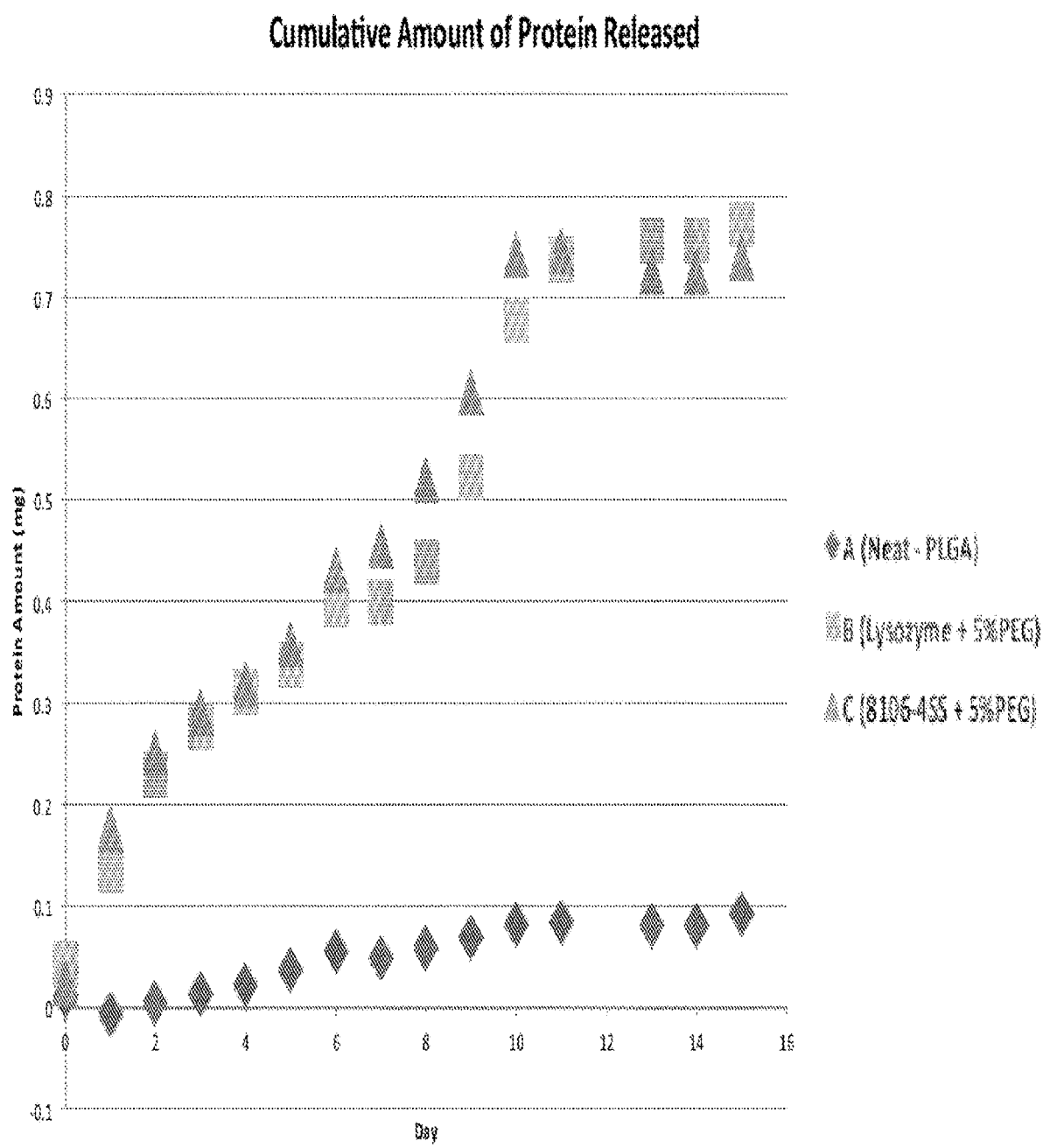
FIG. 4 is a graph showing elution of ultra-stable single-chain analogue (SCI) from PLGA polymer (50-50%) in phosphate-buffered saline (pH 7.4 and 37° C.). Horizontal axis denotes soaking time. Vertical axis denotes nanograms of insulin analogue (dark gray triangles) or relative Bradford-active material in control polymers containing hen egg white lysozyme (light gray squares) or no protein (dark gray diamonds). The latter represents background signal in the Bradford assay due to non-protein material. Horizontal plateau at days 10-15 represents no further elution of protein from the polymers. Samples were made with 5% PEG (mean molecular mass 8 kDa) to optimize the near-linear rate of SCI elution between 1-10 days. Immediate burst release of a portion of the material is not shown.

Whereas little protein was released in the absence of PEG (0%) over the course of 10 days, addition of 10% PEG led to substantial release over 1-2 days. Addition of 5% PEG resulted in a near-linear release of ca. half of the loaded protein over a 10-day period (triangles in FIG. 4; insulin analogue concentrations measured by the Bradford assay as calibrated by ELISA). A similar elution profile was observed in control studies of an analogous co-polymer containing hen egg-white lysozyme instead of an insulin analogue (squares in FIG. 4; arbitrary units). In both cases a horizontal plateau was observed during days 10-15, indicating no further release of the protein from the polymer. The cumulative amounts of protein released are also provided below in Table 1. In this table the micrograms of insulin corresponding to the Bradford assay was verified by ELISA whereas the readings for lysozyme are uncalibrated by an independent assay.

TABLE 1

Cumulative Amount of Protein Released Daily

| Day | A (Neat – PLGA) | B (Lysozyme + 5% PEG) | C (8106-4SS + 5% PEG) |
| --- | --- | --- | --- |
| 0 | 0.0104 | 0.0432 | 0.024 |
| 1 | −0.0071 | 0.135 | 0.1766 |
| 2 | 0.0036 | 0.2289 | 0.2504 |
| 3 | 0.0127 | 0.2759 | 0.2896 |
| 4 | 0.0213 | 0.3104 | 0.3184 |
| 5 | 0.0365 | 0.3383 | 0.3574 |
| 6 | 0.0546 | 0.3978 | 0.4316 |
| 7 | 0.0482 | 0.3987 | 0.455 |
| 8 | 0.0574 | 0.44 | 0.5197 |
| 9 | 0.0679 | 0.5212 | 0.6054 |
| 10 | 0.0809 | 0.6783 | 0.7418 |
| 11 | 0.0828 | 0.7366 | 0.7452 |
| 12 | 0.0795 | 0.7297 | 0.7185 |
| 13 | 0.0802 | 0.7556 | 0.7246 |
| 14 | 0.0802 | 0.7556 | 0.7246 |
| 15 | 0.0915 | 0.7718 | 0.7387 |

The biological activity of the released SCI hormone analogue (in the polymer melts prepared with 5% PEG) was tested in diabetic male Lewis rats (mean weight ca. 300 grams; rendered diabetic by streptozotocin with mean glycemia ca. 400 mg/dl); the blood glucose-lowering activity of the virgin SCI was compared to the activities of the protein eluted after day 1 and day 5. The biological activities of these three samples were indistinguishable, demonstrating that the process of thermal-melt extrusion and graduate release in a physiological buffer at body temperature is not associated with loss of potency.

TABLE 2

| Insulin | Delta per hour for first half hour | SE | Delta per hour for first hour | SE | Number of Animals |
|---|---|---|---|---|---|
| C-1 (PLGA + 25% 4SS-81-06 + 5% PEG; 20 μg) | −320.10 | 48.90 | −315.11 | 6.96 | 2 |
| C-5 (PLGA + 25% 4SS-81-06 + 5% PEG; 5 μg) | −312.60 | 22.20 | −224.36 | 2.36 | 2 |

| Insulin | Percentage of baseline at 30 min | SE | Percentage of baseline at 60 min | SE | Number of Animals |
|---|---|---|---|---|---|
| C-1 (PLGA + 25% 4SS-81-06 + 5% PEG; 20 μg) | 0.6296 | 0.0504 | 0.2964 | 0.0014 | 2 |
| C-5 (PLGA + 25% 4SS-81-06 + 5% PEG; 5 μg) | 0.950 | 0.005 | 0.814 | 0.043 | 2 |

Figure 5:
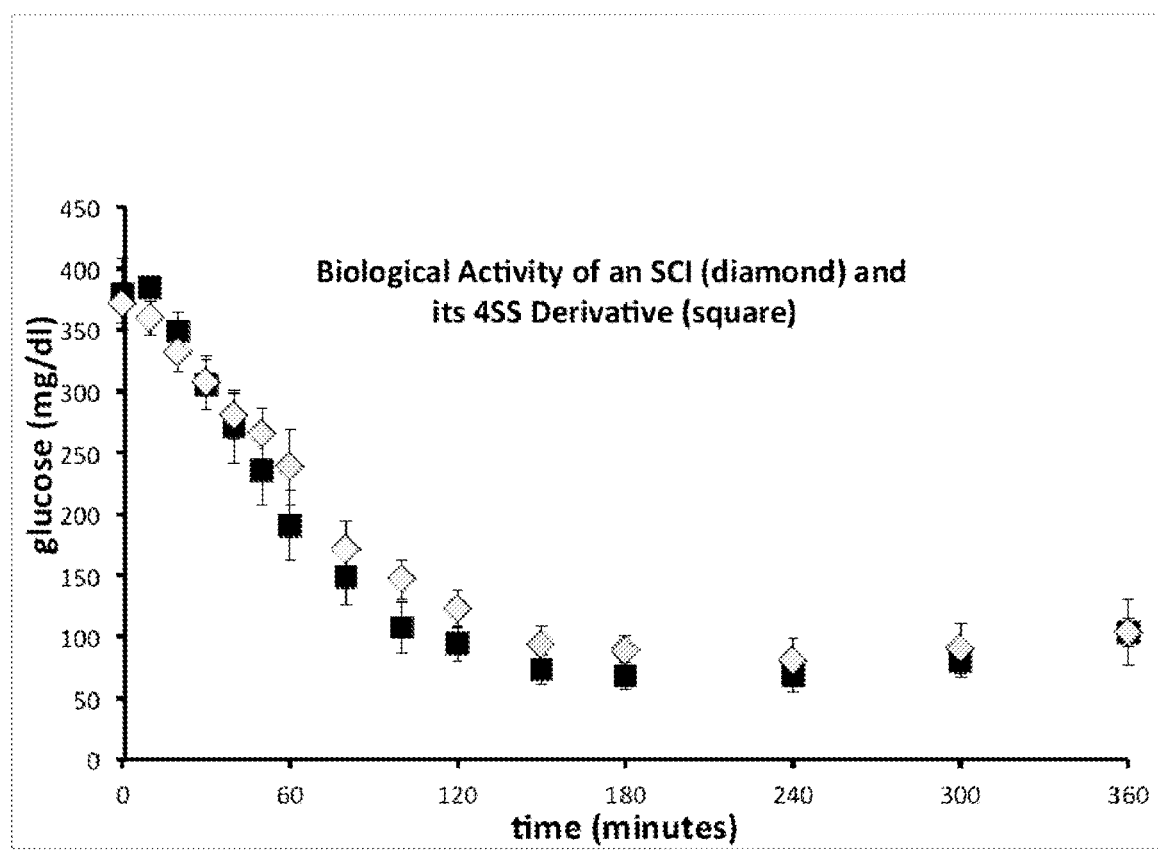
FIG. 5 is a graph showing blood glucose levels over time for 57mer SCIs with (squares; SEQ ID NO: 15) and without (gray diamonds; SEQ ID NO: 16) a fourth disulfide bridge (between residues B4 and A10) over time following subcutaneous injection in diabetic male Lewis rats.

The biological activities of a 57mer SCI (noted as 81-04 herein; SEQ ID NO: 16) and its derivative containing a fourth disulfide bridge (4SS 81-04; SEQ ID NO: 15) were compared. Providing a dose of 20 micrograms per 300 gram rat, the biological activities are essentially identical (see FIG. 5) The sequence of 81-04 is similar to that of SEQ ID NO: 12 except for the absence of $Cys^{A10}$, $Cys^{B4}$; further, residue B28 is Aspartic Acid and residue B29 is Proline. This demonstrates that the introduction of a fourth disulfide bridge into a single-chain insulin analogue molecule does not alter the underlying biological activity of the SCI. This is surprising in view of the prior art, which indicated that in two-chain analogs a marked prolongation of the pharmacodynamic response occurs when introducing the 4th disulfide bridge.

The receptor-binding affinity of analogue 81-04 and analogue 4SS 81-04 was also determined. The affinity of 4SS 81-04 for the A isoform of the insulin receptor was determined to be 120±20 percent relative to human insulin (and may in fact be the same as wild-type human insulin given the error present; data not shown). Its affinity for the B isoform of the insulin receptor is reduced by between fivefold and tenfold relative to wild-type human insulin. This preference for the A isoform is similar to that of the 81-04 parent analogue. Furthermore, the affinity of 4SS 81-04 for the mitogenic IGF Type I receptor (IGF-1R) is reduced by between fivefold and tenfold relative to wild-type human insulin (data not shown). Such impaired binding to IGF-1R is desirable from the perspective of potential carcinogenesis on long-term use.

The sequences of the polypeptides disclosed herein are provided as follows. The amino-acid sequence of human proinsulin is provided, for comparative purposes, as SEQ ID NO: 1.

(human proinsulin)
SEQ ID NO: 1
Phe-Val-Asn-Gln-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Pro-Lys-Thr-Arg-Arg-Glu-Ala-Glu-Asp-
Leu-Gln-Val-Gly-Gln-Val-Glu-Leu-Gly-Gly-Gly-Pro-
Gly-Ala-Gly-Ser-Leu-Gln-Pro-Leu-Ala-Leu-Glu-Gly-
Ser-Leu-Gln-Lys-Arg-Gly-Ile-Val-Glu-Gln-Cys-Cys-
Thr-Ser-Ile-Cys-Ser-Leu-Tyr-Gln-Leu-Glu-Asn-Tyr-
Cys-Asn The amino-acid sequence of the A chain of human insulin is provided as SEQ ID NO: 2.

(human A chain)
SEQ ID NO: 2
Gly-Ile-Val-Glu-Gln-Cys-Cys-Thr-Ser-Ile-Cys-Ser-
Leu-Tyr-Gln-Leu-Glu-Asn-Tyr-Cys-Asn The amino-acid sequence of the B chain of human insulin is provided as SEQ ID NO: 3.

(human B chain)
SEQ ID NO: 3
Phe-Val-Asn-Gln-His-Leu-Cys-Gly-Ser-His-Leu-Val-
Glu-Ala-Leu-Tyr-Leu-Val-Cys-Gly-Glu-Arg-Gly-Phe-
Phe-Tyr-Thr-Pro-Lys-Thr The amino-acid sequence of single-chain insulin analogues of the present invention are given in SEQ ID NO 4, containing a fourth cysteine at positions B4 and A10 and corresponding to polypeptides of length 56, 57, 57, 58, 59, 60, 61, and 62, such that the SCI contains at least one other stabilizing modification at one or more of the indicated positions.

SEQ ID NO: 4
Phe-Val-Asn-Cys-His-Leu-Cys-Gly-Ser-His-Leu-Val-
Glu-Ala-Leu-Tyr-Leu-Val-Cys-Gly-Glu-Arg-Gly-Xaa$_1$-
Phe-Tyr-Thr-Pro-Xaa$_2$-Thr-[foreshortened C
domain]-Gly-Ile-Val-Glu-Gln-Cys-Cys-Xaa$_3$-
Ser-Cys-Cys-Ser-Leu-Xaa$_4$-Gln-Leu-Glu-Asn-
Tyr-Cys-Xaa$_5$ Where $Xaa_1$ indicates Phe or a modification of Phe by a halogen atom (F, Cl or Br) at the ortho or 2-ring position; $Xaa_2$ indicates Glu, Ala, Ile, Leu, Val, Norleucine, aminopropionic acid or amino-butryic acid; where $Xaa_3$ is His, Glu, Lys, Arg, or another non-beta-branched polar or charged amino acid; where $Xaa_4$ is Tyr (as in wild-type insulin), Glu or another non-beta-branched polar or charged amino acid; and optionally where $Xaa_5$ is Gly, Ala, Asp or Ser. The bracketed term "[foreshortened C domain]" designates a connecting peptide domain of length 5-11 residues that contains an acidic residue at either the first (N-terminal) or second peptide position (i.e., residues 31 or 32 of the single-chain insulin analogue). Optionally, $Phe^{B1}$ may be deleted to yield a des-B1 analogue or both Phe$^{B1}$ and Val$^{B2}$ may be omitted to yield a des-[B1, B2] analogue.

The amino-acid sequence of two-chain insulin analogues of the present invention are given in SEQ ID NO 5-8, corresponding to a B chain containing Cysteine at position B4 (SEQ ID NOS: 5, 7 and 8) and an A chain containing Cysteine at position A10 (SEQ ID NO: 6) such that the intact insulin analogue contains a fourth disulfide bridge between positions B4 and A10 and at least one other stabilizing modification at the designated positions.

(Variant B chain):
SEQ ID NO: 5
Phe-Val-Asn-Cys-His-Leu-Cys-Gly-Ser-His-Leu-Val- Glu-Ala-Leu-Tyr-Leu-Val-Cys-Gly-Glu-Arg-Gly-Xaa$_1$-

Phe-Tyr-Thr-Pro-Xaa$_2$-Thr

Where Xaa$_1$ indicates Phe or a modification of Phe by a halogen atom (F, Cl or Br) at the ortho or 2-ring position; Xaa$_2$ indicates Glu, Ala, Ile, Leu, Val, Norleucine, amino-propionic acid or amino-butryic acid;

(Variant A chain):
SEQ ID NO: 6
Gly-Ile-Val-Glu-Gln-Cys-Cys-Xaa$_3$-Ser-Cys-Cys- Ser-Leu-Xaa$_4$-Gln-Leu-Glu-Asn-Tyr-Cys-Xaa$_5$ where Xaa$_3$ is His, Glu, Lys, Arg, or another non-beta-branched polar or charged amino acid; where Xaa$_4$ is Tyr (as in wild-type insulin), Glu or another non-beta-branched polar or charged amino acid; and optionally where Xaa$_5$ is Gly, Ala, Asp or Ser.

(Variant des-[B1]-B chain):
SEQ ID NO: 7
Val-Asn-Cys-His-Leu-Cys-Gly-Ser-His-Leu-Val-Glu- Ala-Leu-Tyr-Leu-Val-Cys-Gly-Glu-Arg-Gly-Xaa$_1$-

Phe-Tyr-Thr-Pro-Xaa$_2$-Thr

Where Xaa$_1$ indicates Phe or a modification of Phe by a halogen atom (F, Cl or Br) at the ortho or 2-ring position; Xaa$_2$ indicates Glu, Ala, Ile, Leu, Val, Norleucine, amino-propionic acid or amino-butryic acid.

(Variant des-[B1, B2]-B chain):
SEQ ID NO: 8
Asn-Cys-His-Leu-Cys-Gly-Ser-His-Leu-Val-Glu-Ala- Leu-Tyr-Leu-Val-Cys-Gly-Glu-Arg-Gly-Xaa$_1$-

Phe-Tyr-Thr-Pro-Xaa$_2$-Thr

Where Xaa$_1$ indicates Phe or a modification of Phe by a halogen atom (F, Cl or Br) at the ortho or 2-ring position; Xaa$_2$ indicates Glu, Ala, Ile, Leu, Val, Norleucine, amino-propionic acid or amino-butryic acid.

Single-Chain Insulin (SCI) analogues are provided as SEQ ID NOs: 9-12, 15 and 16.

SEQ ID NO: 9
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Arg-Thr-Glu-Glu-Gly-Ser-Arg-Arg-

Ser-Arg-Gly-Ile-Val-Glu-Gln-Cys-Cys-Arg-Ser-Ile-

Cys-Ser-Leu-Tyr-Gln-Leu-Glu-Asn-Tyr-Cys-Asn

SEQ ID NO: 10
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Arg-Thr-Glu-Glu-Gly-Ser-Arg-Arg-

Ser-Arg-Gly-Ile-Val-Glu-Gln-Cys-Cys-Arg-Ser-Cys-

Cys-Ser-Leu-Tyr-Gln-Leu-Glu-Asn-Tyr-Cys-Asn

SEQ ID NO: 11
Phe-Val-Asn-Gln-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Glu-Thr-Glu-Glu-Gly-Pro-Arg-Arg-

Gly-Ile-Val-Glu-Gln-Cys-Cys-Glu-Ser-Ile-Cys-Ser-

Leu-Tyr-Gln-Leu-Glu-Asn-Tyr-Cys-Asn (81-066-4SS)
SEQ ID NO: 12
Phe-Val-Asn-Cys-His-Leu-Cys-Gly-Ser-His-Leu-Val-

Glu-Ala-Leu-Tyr-Leu-Val-Cys-Gly-Glu-Arg-Gly-Phe-

Phe-Tyr-Thr-Pro-Glu-Thr-Glu-Glu-Gly-Pro-Arg-Arg-

Gly-Ile-Val-Glu-Gln-Cys-Cys-His-Ser-Cys-Cys-Ser-

Leu-Glu-Gln-Leu-Glu-Asn-Tyr-Cys-Asn (human B chain, KP)
SEQ ID NO: 13
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Lys-Pro-Thr (human B chain, Cys B4, KP)
SEQ ID NO: 14
Phe-Val-Asn-Cys-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Lys-Pro-Thr (4SS 81-04; 57mer)
SEQ ID NO: 15
Phe-Val-Asn-Cys-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Asp-Pro-Thr-Glu-Glu-Gly-Pro-Arg-Arg- Gly-Ile-Val-Glu-Gln-Cys-Cys-His-Ser-Cys-Cys-Ser- Leu-Glu-Gln-Leu-Glu-Asn-Tyr-Cys-Asn (81-04; 57mer)
SEQ ID NO: 16
Phe-Val-Asn-Gln-His-Leu-Cys-Gly-Ser-His-Leu-Val- Glu-Ala-Leu-Tyr-Leu-Val-Cys-Gly-Glu-Arg-Gly-Phe- Phe-Tyr-Thr-Asp-Pro-Thr-Glu-Glu-Gly-Pro-Arg-Arg- Gly-Ile-Val-Glu-Gln-Cys-Cys-His-Ser-Ile-Cys-Ser- Leu-Glu-Gln-Leu-Glu-Asn-Tyr-Cys-Asn Based upon the foregoing disclosure, it should now be apparent that the single-chain insulin analogues provided will carry out the objects set forth hereinabove. Namely, these insulin analogues exhibit enhanced resistance to fibrillation while retaining desirable pharmacokinetic and pharmacodynamic features (conferring prolonged action) and maintaining at least a fraction of the biological activity of wild-type insulin. It is, therefore, to be understood that any variations evident fall within the scope of the claimed invention and thus, the selection of specific component elements can be determined without departing from the spirit of the invention herein disclosed and described.

The following literature is cited to demonstrate that the testing and assay methods described herein would be understood by one of ordinary skill in the art.

Ahmed, T. 2015. Review: approaches to develop PLGA based in situ gelling system with low initial burst. *Pak. J Pharm. Sci.* 28:657-65.

Hohsaka, T., & Sisido, M. 2012. Incorporation of non-natural amino acids into proteins. *Curr. Opin. Chem. Biol.* 6, 809-15.

Hua, Q. X., Nakagawa, S. H., Jia, W., Huang, K., Phillips, N. B., Hu, S. & Weiss, M. A. (2008) Design of an active ultrastable single-chain insulin analog: synthesis, structure, and therapeutic implications. *J. Biol. Chem.* 283, 14703-14716.

Kristensen, C., Andersen, A. S., Hach, M., Wiberg, F. C., Schäffer, L., & Kjeldsen, T. 1995. A single-chain insulin-like growth factor I/insulin hybrid binds with high affinity to the insulin receptor. *Biochem. J.* 305, 981-6.

Lee, H. C., Kim, S. J., Kim, K. S., Shin, H. C., & Yoon, J. W. 2000. Remission in models of type 1 diabetes by gene therapy using a single-chain insulin analogue. *Nature* 408, 483-8. Retraction in: Lee H C, Kim K S, Shin H C. 2009. *Nature* 458, 600.

Lee, P, Towslee J, Maia J, and Pokorski J. 2015. PEGylation to Improve Protein Stability During Melt Processing. *Macromol. Biosci.* 15:1332-7.

Ortega-Oller, I, Padial-Molina M, Galindo-Moreno P, O'Valle F, Jódar-Reyes A B, and Peula-Garcia J M. 2015. Bone Regeneration from PLGA Micro-Nanoparticles. *Biomed. Res. Int* 2015:415289.

Phillips, N. B., Whittaker, J., Ismail-Beigi, F., & Weiss, M. A. (2012) Insulin fibrillation and protein design: topological resistance of single-chain analogues to thermal degradation with application to a pump reservoir. *J. Diabetes Sci. Technol.* 6, 277-288.

Rahimian, S., Fransen M F, Kleinovink J W, Amidi M, Ossendorp F, and Hennink W E. 2015. Particulate Systems Based on Poly(Lactic-co-Glycolic)Acid (pLGA) for Immunotherapy of Cancer. *Curr. Pharm. Des.* 21:4201-16.

Vinther T N, Pettersson I, Huus K, Schlein M, Steensgaard D B, Sorensen A, Jensen K J, Kjeldsen T, and Hubalek F. 2015. Additional disulfide bonds in insulin: Prediction, recombinant expression, receptor binding affinity, and stability. *Protein Sci.* 24:779-88.

Vinther T N, Norrman M, Ribel U, Huus K, Schlein M, Steensgaard D B, Pedersen T A, Pettersson I, Ludvigsen S, Kjeldsen T, Jensen K J, and Hubalek F. 2013. Insulin analog with additional disulfide bond has increased stability and preserved activity. *Protein Sci.* 22:296-305.

Wang, Z. X. 1995. An exact mathematical expression for describing competitive biding of two different ligands to a protein molecule *FEBS Lett* 360: 111-114.

Whittaker, J., and Whittaker, L. 2005. Characterization of the functional insulin binding epitopes of the full-length insulin receptor. *J. Biol. Chem.* 280: 20932-20936.

What is claimed is:

1. An insulin composition comprising an insulin analogue and a polymer blend, wherein the insulin analogue contains cysteine substitutions at positions corresponding to residues B4 and A10 relative to wild type insulin, a connecting domain of 5-11 amino acids between A and B domains of the insulin analogue, wherein the insulin analogue comprises Glutamic acid at at least one of the first two positions of the connecting domain, and wherein the insulin analogue contains at least one of:
   (a) an alanine, histidine, glutamic acid or arginine substitution at a position corresponding to position A8 of wild type insulin; and
   (b) an alanine, glutamic acid or arginine substitution at a position corresponding to position A14 of wild type insulin.

2. The insulin composition of claim 1 wherein the polymer is comprised of poly(lactic-co-glycolic acid) (PL-GA).

3. The insulin composition of claim 2 wherein the polymer is comprised of poly(lactic-co-glycolic acid) (PL-GA) such that the percentage of poly lactic acid is between 25 and 75%.

4. The insulin composition of claim 3 wherein the polymer is comprised of poly(lactic-co-glycolic acid) (PL-GA) such that the percentage of poly lactic acid is 50%.

5. The insulin composition of claim 2, additionally comprising free Polyethylene glycol.

6. The insulin composition of claim 1 wherein the insulin analogue has a sequence selected from the group consisting of SEQ ID NOs: 10, 12 and 15.

7. The insulin composition of claim 1, wherein the insulin analogue comprises SEQ ID NO: 5.

8. The insulin composition of claim 7, additionally comprising SEQ ID NO: 6.

9. The insulin composition of claim 1, wherein the insulin composition is fabricated into a microneedle patch adapted for topical application.

10. The insulin composition of claim 1, wherein the insulin composition is fabricated into a suspension of microbeads adapted for subcutaneous injection.

11. A method for the treatment of diabetes mellitus in a human patient or a mammal, the method comprising administration of an insulin composition comprising an insulin analogue and a polymer blend, wherein the insulin analogue contains cysteine substitutions at positions corresponding to residues B4 and A10 relative to wild type insulin, a connecting domain of 5-11 amino acids between A and B domains of the insulin analogue, wherein the insulin analogue comprises Glutamic acid at at least one of the first two positions of the connecting domain, and wherein the insulin analogue contains at least one of:
   (a) an alanine, histidine, glutamic acid or arginine substitution at a position corresponding to position A8 of wild type insulin;
   (b) an alanine, glutamic acid or arginine substitution at a position corresponding to position A14 of wild type insulin.

12. The method of claim 11 wherein the insulin composition is administered by a device attached to the skin.

13. The method of claim 11 wherein the insulin composition is administered by the subcutaneous injection.

14. The method of claim 11, wherein the insulin analogue has a sequence selected from the group consisting of SEQ ID NOs: 10, 12 and 15.

15. The method of claim 11, wherein the insulin analogue comprises SEQ ID NO: 5.

* * * * *

SEQUENCE LISTING

```
<160> NUMBER OF SEQ ID NOS: 16

<210> SEQ ID NO 1
<211> LENGTH: 86
<212> TYPE: PRT
<213> ORGANISM: Homo sapiens

<400> SEQUENCE: 1

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr Arg Arg
            20                  25                  30

Glu Ala Glu Asp Leu Gln Val Gly Gln Val Glu Leu Gly Gly Gly Pro
        35                  40                  45

Gly Ala Gly Ser Leu Gln Pro Leu Ala Leu Glu Gly Ser Leu Gln Lys
    50                  55                  60

Arg Gly Ile Val Glu Gln Cys Cys Thr Ser Ile Cys Ser Leu Tyr Gln
65                  70                  75                  80

Leu Glu Asn Tyr Cys Asn
                85

<210> SEQ ID NO 2
<211> LENGTH: 21
<212> TYPE: PRT
<213> ORGANISM: Homo sapiens

<400> SEQUENCE: 2
```

Gly Ile Val Glu Gln Cys Cys Thr Ser Ile Cys Ser Leu Tyr Gln Leu
1               5                   10                  15

Glu Asn Tyr Cys Asn
            20

<210> SEQ ID NO 3
<211> LENGTH: 30
<212> TYPE: PRT
<213> ORGANISM: Homo sapiens

<400> SEQUENCE: 3

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Lys Thr
            20                  25                  30

<210> SEQ ID NO 4
<211> LENGTH: 62
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Phe or an ortho halogenated Phe
<220> FEATURE:
<221> NAME/KEY: MISC_FEATURE
<222> LOCATION: (29)..(29)
<223> OTHER INFORMATION: Xaa is Glu, Ala, Ile, Leu, Val, Norleucine,
      amino propionic acid or amino butryic acid
<220> FEATURE:
<221> NAME/KEY: MISC_FEATURE
<222> LOCATION: (31)..(41)
<223> OTHER INFORMATION: Xaa is 5 11 of any amino acid with the provison
      that the Xaa at 31 or 32 contains an acidic amino acid
<220> FEATURE:
<221> NAME/KEY: MISC_FEATURE
<222> LOCATION: (49)..(49)
<223> OTHER INFORMATION: Xaa is His, Glu, Lys, Arg, or another non beta
      branched polar or charged amino acid
<220> FEATURE:
<221> NAME/KEY: MISC_FEATURE
<222> LOCATION: (55)..(55)
<223> OTHER INFORMATION: Xaa is Tyr, Glu or another non beta branched
      polar or charged amino acid
<220> FEATURE:
<221> NAME/KEY: MISC_FEATURE
<222> LOCATION: (62)..(62)
<223> OTHER INFORMATION: Xaa is Asn, Gly, Ala, Asp or Ser

<400> SEQUENCE: 4

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Xaa Thr Xaa Xaa
            20                  25                  30

Xaa Xaa Xaa Xaa Xaa Xaa Xaa Xaa Gly Ile Val Glu Gln Cys Cys
        35                  40                  45

Xaa Ser Cys Cys Ser Leu Xaa Gln Leu Glu Asn Tyr Cys Xaa
    50                  55                  60

<210> SEQ ID NO 5
<211> LENGTH: 30
<212> TYPE: PRT
<213> ORGANISM: Homo sapiens
<220> FEATURE:
<221> NAME/KEY: MISC_FEATURE
<222> LOCATION: (24)..(24)
<223> OTHER INFORMATION: Xaa is Phe or an ortho halogenated Phe
<220> FEATURE:
<221> NAME/KEY: MISC_FEATURE

```
<222> LOCATION: (29)..(29)
<223> OTHER INFORMATION: Xaa is Glu, Ala, Ile, Leu, Val, Norleucine,
      amino propionic acid or amino butryic acid

<400> SEQUENCE: 5

Phe Val Asn Cys His Leu Cys Gly Ser His Leu Val Glu Ala Leu Tyr
1               5                   10                  15

Leu Val Cys Gly Glu Arg Gly Xaa Phe Tyr Thr Pro Xaa Thr
            20                  25                  30

<210> SEQ ID NO 6
<211> LENGTH: 21
<212> TYPE: PRT
<213> ORGANISM: Homo sapiens
<220> FEATURE:
<221> NAME/KEY: MISC_FEATURE
<222> LOCATION: (8)..(8)
<223> OTHER INFORMATION: Xaa is His, Glu, Lys, Arg, or another non beta
      branched polar or charged amino acid
<220> FEATURE:
<221> NAME/KEY: MISC_FEATURE
<222> LOCATION: (14)..(14)
<223> OTHER INFORMATION: Xaa is Tyr, Glu or another non beta branched
      polar or charged amino acid
<220> FEATURE:
<221> NAME/KEY: MISC_FEATURE
<222> LOCATION: (21)..(21)
<223> OTHER INFORMATION: Xaa is Asn, Gly, Ala, Asp or Ser

<400> SEQUENCE: 6

Gly Ile Val Glu Gln Cys Cys Xaa Ser Cys Cys Ser Leu Xaa Gln Leu
1               5                   10                  15

Glu Asn Tyr Cys Xaa
            20

<210> SEQ ID NO 7
<211> LENGTH: 29
<212> TYPE: PRT
<213> ORGANISM: Homo sapiens
<220> FEATURE:
<221> NAME/KEY: MISC_FEATURE
<222> LOCATION: (23)..(23)
<223> OTHER INFORMATION: Xaa is Phe or an ortho halogenated Phe
<220> FEATURE:
<221> NAME/KEY: MISC_FEATURE
<222> LOCATION: (28)..(28)
<223> OTHER INFORMATION: Xaa is Glu, Ala, Ile, Leu, Val, Norleucine,
      amino propionic acid or amino butryic acid

<400> SEQUENCE: 7

Val Asn Cys His Leu Cys Gly Ser His Leu Val Glu Ala Leu Tyr Leu
1               5                   10                  15

Val Cys Gly Glu Arg Gly Xaa Phe Tyr Thr Pro Xaa Thr
            20                  25

<210> SEQ ID NO 8
<211> LENGTH: 28
<212> TYPE: PRT
<213> ORGANISM: Homo sapiens
<220> FEATURE:
<221> NAME/KEY: MISC_FEATURE
<222> LOCATION: (22)..(22)
<223> OTHER INFORMATION: Xaa is Phe or an ortho halogenated Phe
<220> FEATURE:
<221> NAME/KEY: MISC_FEATURE
<222> LOCATION: (27)..(27)
<223> OTHER INFORMATION: Xaa is Glu, Ala, Ile, Leu, Val, Norleucine,
      amino propionic acidor amino butryic acid

<400> SEQUENCE: 8
```

Asn Cys His Leu Cys Gly Ser His Leu Val Glu Ala Leu Tyr Leu Val
1               5                   10                  15

Cys Gly Glu Arg Gly Xaa Phe Tyr Thr Pro Xaa Thr
            20                  25

<210> SEQ ID NO 9
<211> LENGTH: 59
<212> TYPE: PRT
<213> ORGANISM: Homo sapiens

<400> SEQUENCE: 9

Phe Val Asn Gln His Leu Cys Gly Ser His Leu Val Glu Ala Leu Tyr
1               5                   10                  15

Leu Val Cys Gly Glu Arg Gly Phe Phe Tyr Thr Pro Arg Thr Glu Glu
            20                  25                  30

Gly Ser Arg Arg Ser Arg Gly Ile Val Glu Gln Cys Cys Arg Ser Ile
        35                  40                  45

Cys Ser Leu Tyr Gln Leu Glu Asn Tyr Cys Asn
    50                  55

<210> SEQ ID NO 10
<211> LENGTH: 59
<212> TYPE: PRT
<213> ORGANISM: Homo sapiens

<400> SEQUENCE: 10

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Arg Thr Glu Glu
            20                  25                  30

Gly Ser Arg Arg Ser Arg Gly Ile Val Glu Gln Cys Cys Arg Ser Cys
        35                  40                  45

Cys Ser Leu Tyr Gln Leu Glu Asn Tyr Cys Asn
    50                  55

<210> SEQ ID NO 11
<211> LENGTH: 57
<212> TYPE: PRT
<213> ORGANISM: Homo sapiens

<400> SEQUENCE: 11

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Glu Thr Glu Glu
            20                  25                  30

Gly Pro Arg Arg Gly Ile Val Glu Gln Cys Cys Glu Ser Cys Cys Ser
        35                  40                  45

Leu Tyr Gln Leu Glu Asn Tyr Cys Asn
    50                  55

<210> SEQ ID NO 12
<211> LENGTH: 57
<212> TYPE: PRT
<213> ORGANISM: Homo sapiens

<400> SEQUENCE: 12

Phe Val Asn Cys His Leu Cys Gly Ser His Leu Val Glu Ala Leu Tyr
1               5                   10                  15

Leu Val Cys Gly Glu Arg Gly Phe Phe Tyr Thr Pro Glu Thr Glu Glu 20                  25                  30

Gly Pro Arg Arg Gly Ile Val Glu Gln Cys Cys His Ser Cys Cys Ser
                35                  40                  45

Leu Glu Gln Leu Glu Asn Tyr Cys Asn
            50                  55

<210> SEQ ID NO 13
<211> LENGTH: 30
<212> TYPE: PRT
<213> ORGANISM: Homo sapiens

<400> SEQUENCE: 13

Phe Val Asn Gln His Leu Cys Gly Ser His Leu Val Glu Ala Leu Tyr
1               5                   10                  15

Leu Val Cys Gly Glu Arg Gly Phe Phe Tyr Thr Lys Pro Thr
                20                  25                  30

<210> SEQ ID NO 14
<211> LENGTH: 30
<212> TYPE: PRT
<213> ORGANISM: Homo sapiens

<400> SEQUENCE: 14

Phe Val Asn Cys His Leu Cys Gly Ser His Leu Val Glu Ala Leu Tyr
1               5                   10                  15

Leu Val Cys Gly Glu Arg Gly Phe Phe Tyr Thr Lys Pro Thr
                20                  25                  30

<210> SEQ ID NO 15
<211> LENGTH: 57
<212> TYPE: PRT
<213> ORGANISM: Homo sapiens

<400> SEQUENCE: 15

Phe Val Asn Cys His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
                20                  25                  30

Gly Pro Arg Arg Gly Ile Val Glu Gln Cys Cys His Ser Cys Cys Ser
                35                  40                  45

Leu Glu Gln Leu Glu Asn Tyr Cys Asn
            50                  55

<210> SEQ ID NO 16
<211> LENGTH: 57
<212> TYPE: PRT
<213> ORGANISM: Homo sapiens

<400> SEQUENCE: 16

Phe Val Asn Gln His Leu Cys Gly Ser His Leu Val Glu Ala Leu Tyr
1               5                   10                  15

Leu Val Cys Gly Glu Arg Gly Phe Phe Tyr Thr Asp Pro Thr Glu Glu
                20                  25                  30

Gly Pro Arg Arg Gly Ile Val Glu Gln Cys Cys His Ser Ile Cys Ser
                35                  40                  45

Leu Glu Gln Leu Glu Asn Tyr Cys Asn
            50                  55